US00PP25464P2

(12) United States Plant Patent
Dummen

(10) Patent No.: US PP25,464 P2
(45) Date of Patent: Apr. 21, 2015

(54) ***BACOPA* PLANT NAMED 'DUEBAHPIHAL'**

(50) Latin Name: *Bacopa hybrida*
Varietal Denomination: Duebahpihal

(71) Applicant: Tobias Dummen, Rheinberg (DE)

(72) Inventor: Tobias Dummen, Rheinberg (DE)

(73) Assignee: Dümmen Group B.V., De Lier (NL)

( * ) Notice: Subject to any disclaimer, the term of this patent is extended or adjusted under 35 U.S.C. 154(b) by 60 days.

(21) Appl. No.: 13/987,089

(22) Filed: Jul. 1, 2013

(51) Int. Cl.
*A01H 5/00* (2006.01)

(52) U.S. Cl.
USPC ..... Plt./485

(58) Field of Classification Search
USPC ..... Plt./485
See application file for complete search history.

*Primary Examiner* — Kent L Bell
(74) *Attorney, Agent, or Firm* — C. A. Whealy

(57) ABSTRACT

A new and distinct cultivar of *Bacopa* plant named 'Duebahpihal', characterized by its compact, mounding and trailing growth habit; vigorous growth habit; freely branching habit; freely flowering habit; and light pink-colored flowers with darker pink-colored centers.

1 Drawing Sheet

Botanical designation: *Bacopa hybrida.*
Cultivar denomination: 'DUEBAHPIHAL'.

CROSS-REFERENCED TO CLOSELY RELATED APPLICATIONS

Title: *Bacopa* Plant Named 'DUEBAHPISAN'.
Applicant: Tobias Dümmen.
Filed: Concurrently with this application, U.S. Plant patent application Ser. No. 13/987,091.

BACKGROUND OF THE INVENTION

The present invention relates to a new and distinct cultivar of *Bacopa* plant, botanically known as *Bacopa hybrida* and hereinafter referred to by the name 'Duebahpihal'.

The new *Bacopa* plant is a product of a planned breeding program conducted by the Inventor in Rheinberg, Germany. The objective of the breeding program is to create new compact *Bacopa* plants with numerous pink-colored flowers.

The new *Bacopa* plant originated from a cross-pollination made by the Inventor in Rheinberg, Germany in July, 2010 of a proprietary selection of *Bacopa hybrida* identified as code number F-1902-016, not patented, as the female, or seed, parent with a proprietary selection of *Bacopa hybrida* identified as code number F-1907-162, not patented, as the male, or pollen, parent. The new *Bacopa* plant was discovered and selected by the Inventor as a flowering plant from within the progeny of the stated cross-pollination in a controlled greenhouse environment in Rheinberg, Germany in May, 2012.

Asexual reproduction of the new *Bacopa* plant by cuttings in a controlled greenhouse environment in Rheinberg, Germany since June, 2012, has shown that the unique features of this new *Bacopa* plant are stable and reproduced true to type in successive generations.

SUMMARY OF THE INVENTION

Plants of the new *Bacopa* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Duebahpihal'. These characteristics in combination distinguish 'Duebahpihal' as a new and distinct *Bacopa* plant:

1. Compact, mounding and trailing growth habit.
2. Vigorous growth habit.
3. Freely branching habit.
4. Freely flowering habit.
5. Light pink-colored flowers with darker pink-colored centers.

Plants of the new *Bacopa* can be compared to plants of the female parent selection. Plants of the new *Bacopa* differ primarily from plants of the female parent selection in plant habit as plants of the new *Bacopa* are more compact than plants of the female parent selection. In addition, plants of the new *Bacopa* have darker pink-colored flowers than plants of the female parent selection.

Plants of the new *Bacopa* can be compared to plants of the male parent selection. Plants of the new *Bacopa* differ primarily from plants of the male parent selection in flower color as plants of the new *Bacopa* have lighter pink-colored flowers than plants of the male parent selection.

Plants of the new *Bacopa* can be compared to plants of *Bacopa hybrida* 'Duebahpisan', disclosed in a U.S. Plant Patent application filed concurrently, 13/987,091. Plants of the new *Bacopa* differ primarily from plants of 'Duebahpisan' in flower color as plants of the new *Bacopa* have lighter pink-colored flowers than plants of 'Duebahpisan'.

Plants of the new *Bacopa* also can be compared to plants of the *Bacopa* 'Scopia Great Pink Ring', not patented. In side-by-side comparisons conducted in Rheinberg, Germany, plants of the new *Bacopa* differed primarily from plants of 'Scopia Great Pink Ring' in the following characteristics:

1. Plants of the new *Bacopa* were larger than plants of 'Scopia Great Pink Ring'.
2. Plants of the new *Bacopa* had slightly larger leaves than plants of 'Scopia Great Pink Ring'.

3. Plants of the new *Bacopa* were more freely flowering than plants of 'Scopia Great Pink Ring'.

BRIEF DESCRIPTION OF THE PHOTOGRAPH

The accompanying colored photograph illustrates the overall appearance of the new *Bacopa* plant showing the colors as true as it is reasonably possible to obtain in colored reproductions of this type. Colors in the photograph may differ slightly from the color values cited in the detailed botanical description which accurately describe the colors of the new *Bacopa* plant.

The photograph comprises a close-up view of a typical flowering plant of 'Duebahpihal'.

DETAILED BOTANICAL DESCRIPTION

The aforementioned photograph and following observations, measurements and values describe plants grown during the summer in 10.5-cm containers in a glass-covered greenhouse in Rheinberg, Germany and under cultural practices typical of commercial *Bacopa* production. During the production of the plants, day and night temperatures averaged 18° C. and light levels averaged 4,500 lux. Plants were pinched one time three weeks after planting and were 13 weeks old when the photograph and the description were taken. In the description, color references are made to The Royal Horticultural Society Colour Chart, 1995 Edition, except where general terms of ordinary dictionary significance are used.

Botanical classification: *Bacopa hybrida* 'Duebahpihal'.

Parentage:

*Female, or seed, parent*.—Proprietary selection of *Bacopa hybrida* identified as code number F-1902-016, not patented.

*Male or pollen parent*.—Proprietary selection of *Bacopa hybrida* identified as code number F-1907-162, not patented.

Propagation:

*Type*.—By cuttings.

*Time to initiate roots, summer*.—About five days at temperatures of 20° C.

*Time to initiate roots, winter*.—About seven days at temperatures of 20° C.

*Time to produce a rooted young plant, summer*.—About three weeks at temperatures of 20° C.

*Time to produce a rooted young plant, winter*.—About four weeks at temperatures of 20° C.

*Root description*.—Fine, fibrous; white in color.

*Rooting habit*.—Freely branching; dense.

Plant description:

*Plant and growth habit*.—Compact, mounded and trailing plant habit; vigorous growth habit.

*Branching habit*.—Freely branching habit about six to eight lateral branches develop per plant; pinching enhances branching potential.

*Plant height*.—About 14.5 cm.

*Plant diameter* (*area of spread*).—About 54.5 cm.

Lateral branch description:

*Length*.—About 25.8 cm.

*Diameter*.—About 2.2 mm.

*Internode length*.—About 2.1 cm.

*Strength*.—Strong.

*Texture*.—Pubescent.

*Color*.—Close to 143B.

Leaf description:

*Arrangement*.—Opposite, simple.

*Length*.—About 2.2 cm.

*Width*.—About 2.4 cm.

*Shape*.—Ovate.

*Apex*.—Acuminate.

*Base*.—Obtuse.

*Margin*.—Crenulate.

*Texture, upper and lower surfaces*.—Sparsely pubescent.

*Venation pattern*.—Pinnate.

*Color*.—Developing and fully expanded leaves, upper surface: Close to 144A; venation, close to 144A. Developing and fully expanded leaves, lower surface: Close to 144B; venation, close to 144A.

*Petioles*.—Length: About 7.6 mm. Diameter: About 2.4 mm. Texture, upper and lower surfaces: Pubescent. Color, upper surface: Close to 144A. Color, lower surface: Close to 144B.

Flower description:

*Flower arrangement*.—Single rotate flowers; freely flowering habit with potentially about 170 to 190 flowers developing per plant; flowers face mostly upright.

*Fragrance*.—None detected.

*Natural flowering season*.—Plants begin flowering about six weeks after planting and flower continuously year-round in moderate climates.

*Flower longevity*.—Flowers last about one week on the plant; flowers not persistent.

*Flower diameter*.—About 2.2 cm.

*Flower length* (*height*).—About 1 cm.

*Throat diameter*.—About 5 mm.

*Tube length:*.—About 9.4 mm.

*Flower buds*.—Length: About 7.4 mm. Diameter: About 5.2 mm. Shape: Spatulate. Color: Close to 73D.

*Petals*.—Quantity per flower: Corolla consists of five petals fused at the base. Lobe length: About 8.6 mm. Lobe width: About 7.1 mm. Lobe shape: Obovate. Lobe apex: Obtuse, rounded. Lobe margin: Entire. Texture: Petal lobes, upper and lower surfaces: Smooth, glabrous. Throat: Smooth, glabrous. Tube: Smooth, glabrous. Color: Petal lobes, when opening and fully opened, upper surface: Close to 73D; towards the base, close to 74C; color does not change with development. Petal lobes, when opening and fully opened, lower surface: Close to 73D; color does not change with development. Throat: Close to 24A. Tube: Close to 163B.

*Sepals*.—Appearance: Five sepals fused into a tubular calyx. Length: About 6.2 mm. Width: About 1 mm. Shape: Lanceolate. Apex: Acute. Margin: Entire. Texture, upper and lower surfaces: Smooth, glabrous. Color, upper surface: Close to 144A. Color, lower surface: Close to 144B.

*Peduncles*.—Length: About 1.3 cm. Diameter: About 1 mm. Angle: Erect. Strength: Strong. Texture: Smooth, glabrous. Color: Close to 137C.

*Reproductive organs*.—Androecium: Stamen number: About four. Filament length: About 1.2 cm. Filament color: Close to 155B. Anther shape: Cylindrical. Anther length: About 1.5 mm. Anther color: Close to 17A. Amount of pollen: Abundant. Pollen color: Close to 15B. Gynoecium: Pistil length: About 9 mm.

Style length: About 7 mm. Style color: Close to 144D. Stigma color: Close to 144B. Ovary color: Close to 144B.

*Seeds & fruits*.—Seed and fruit production have not been observed on plants of the new *Bacopa*.

Temperature tolerance: Plants of the new *Bacopa* have been observed to tolerate temperatures from about 5° C. to about 40° C.

Pathogen & pest resistance: Plants of the new *Bacopa* have not been shown to be resistant to pathogens and pests common to *Bacopa* plants.

It is claimed:

1. A new and distinct *Bacopa* plant named 'Duebahpihal' as illustrated and described.

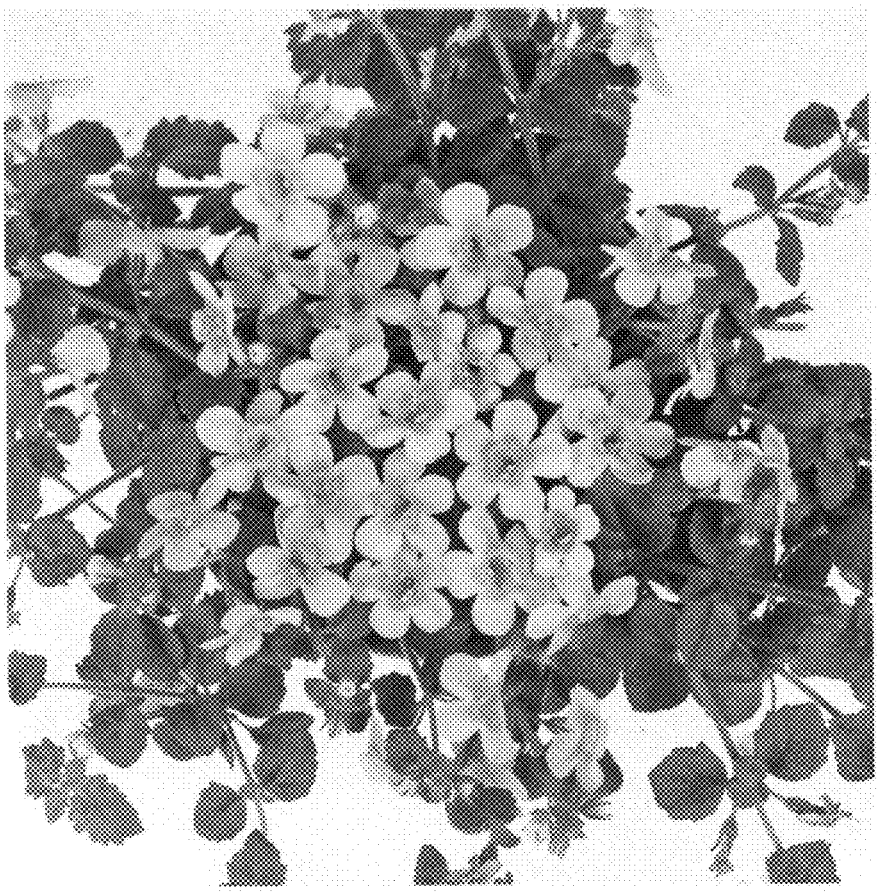

* * * * *